United States Patent [19]

Ebersole et al.

[11] Patent Number: 5,369,011
[45] Date of Patent: Nov. 29, 1994

[54] METHOD AND APPARATUS FOR COLLECTING AND DETECTING BACTERIA

[75] Inventors: Richard C. Ebersole, Wilmington, Del.; Frank T. Gelormini, Gibbstown, N.J.

[73] Assignee: E. I. Du Pont de Nemours and Company, Wilmington, Del.

[21] Appl. No.: 899,824

[22] Filed: Jun. 16, 1992

Related U.S. Application Data

[63] Continuation of Ser. No. 169,718, Mar. 21, 1988, abandoned.

[51] Int. Cl.$^5$ .............................................. C12Q 1/08
[52] U.S. Cl. .................... 435/7.32; 435/7.2; 435/7.92; 435/9; 435/29; 435/30; 435/34; 435/39; 435/40; 435/261; 210/667; 210/671; 210/691; 210/290
[58] Field of Search .............. 435/7.2, 7.32, 7.92, 435/9, 29, 30, 34, 39, 40, 259, 261, 50; 210/667, 671, 691, 290

[56] References Cited

U.S. PATENT DOCUMENTS

| | | | |
|---|---|---|---|
| 3,899,394 | 8/1975 | Willner et al. | 435/50 |
| 3,969,501 | 7/1976 | Shoji et al. | 435/132 |
| 4,116,828 | 9/1978 | Sawyer, Jr. | 210/691 |
| 4,139,456 | 2/1979 | Yabuuchi et al. | 210/722 |
| 4,503,149 | 3/1985 | Boyd | 435/39 |
| 4,515,697 | 5/1985 | Elmaleh et al. | 210/768 |
| 4,543,328 | 9/1985 | Keller et al. | 435/30 |
| 4,592,994 | 6/1986 | Mattiasson | 435/29 |
| 4,765,892 | 8/1988 | Hulbert et al. | 210/290 |
| 4,775,635 | 10/1988 | Ebersole et al. | 436/180 |
| 4,999,286 | 3/1991 | Gawel et al. | 435/7.32 |

FOREIGN PATENT DOCUMENTS

| | | |
|---|---|---|
| 0198413 | 10/1986 | European Pat. Off. . |
| 0272916 | 6/1988 | European Pat. Off. . |
| 2189317 | 10/1987 | United Kingdom . |
| 8301257 | 4/1983 | WIPO .............. 435/261 |
| 8700199 | 1/1987 | WIPO . |

OTHER PUBLICATIONS

Langé et al., J. Am. Water Works Assoc., 78:76–84 (1986).
Lee et al., Lab Pract., 23:297–298 (1974).
Dicalite Filter Aids General Information Sheet: DICALITE 4200.

Primary Examiner—Esther M. Kepplinger
Assistant Examiner—Lora M. Green

[57] ABSTRACT

This invention relates to a method for collecting, concentrating and detecting microorganisms from difficult-to-separate environmental samples e.g. oil well samples and the like, for the purpose of their analysis or identification; and apparatus for performing the method.

7 Claims, 1 Drawing Sheet

METHOD AND APPARATUS FOR COLLECTING AND DETECTING BACTERIA

This is a continuation, of application Ser. No. 07/169,718 filed Mar. 21, 1988, now abandoned.

FIELD OF THE INVENTION

This invention relates to a method for collecting, concentrating and recovering microorganisms from difficult-to-separate environmental samples e.g. oil well samples and the like, for the purpose of their analysis or identification; and apparatus for performing the method.

BACKGROUND OF THE INVENTION

Environmental microbial contamination results in losses of millions of dollars in equipment and product failure each year. Product deterioration, fouling, corrosion, adulteration, and diminished heat transfer capacity have all been attributed to microbial contamination. As an aid in monitoring and controlling detrimental microbial populations, there is a need for a simple sample processing technology which can be used in the field to concentrate and recover microorganisms.

Sulfate-reducing bacteria (SRB), by way of example, are among the most destructive environmental organisms. They cause corrosion and stress cracking of metals used in petroleum production and refining, (C. O. Obuekwe et al., Applied Microbiol. Biotechnol., 26, 389–393, (1987)) cooling water systems, (J. W. McCroy, in Microbiology of Cooling Tower Water, Chemical Publishing Company, New York, (1980)), waste treatment systems, (G. Kobrin et al., Waste Water Treatment Tank, Case Histories, compiled by R. E. Tatnall, Materials Performance, 20, 41–48, (1981)), pulp and paper production (A. Piluso, Materials Performance, 20, 41–48 (1981)). SRB produce hydrogen sulfide, which is more lethal than hydrogen cyanide. The sulfide products can also be used by other organisms to manufacture sulfuric acid, (P. Bos et al., Microbiology of Sulfur-Oxidizing Bacteria, in The Metal Society, 18–27, (1983)), which in turn can rapidly destroy concrete municipal sewage systems. Infestation of waterways by SRB organisms, (J. R. Postgate, in The Sulfate-Reducing Bacteria, 2nd Edition, Cambridge University Press, New York, (1984)), is becoming a serious problem, being both a symptom of oxygen depletion and a problem because of generation of toxic hydrogen sulfide. The combined effect of oxygen depletion and toxic concentrations of hydrogen sulfide suppresses marine life.

Until recently, microbiological detection of environmental microorganisms was limited to laboratory culture. Generally, culture methods are slow, requiring days or weeks to accomplish and are not suited to field testing where control of the organisms is needed. Culture methods have thus been of limited value in monitoring and controlling microbial populations. Many newer direct detection methods developed to accelerate or eliminate culture methods are also fraught with difficulties because of sample complexity, microorganism diversity and analytical insensitivity.

Environmental samples such as soil, sewage, surface water and, particularly, crude oil are complex mixtures which are heterogeneous in both their solid and soluble components. In composition, the samples sometimes contain high concentrations of solid sediments, colloids, emulsions, soluble and insoluble salts, biopolymers, biodegraded debris, inert materials and contaminating industrial and natural chemicals. The heterogeneity and complexity of environmental samples can prevent or invalidate direct detection methods. Microorganisms can adhere to particulates, rendering the microorganisms inaccessible to detection by conventional approaches which rely on liquid filtrate samples. Also chemicals and solutes contained within the samples can interfere or inhibit test methods. Sample coloration, for example, can obstruct test results when colors are part of the assay.

Direct detection of microorganisms and/or their products is further complicated by the fact that in many instances, sample materials contain only small numbers of microorganisms ($10^2$ to $10^5$ cells/gm). Furthermore, in many cases the microorganisms do not comprise a single strain or even a single genus but are a diverse collection of many different types of organisms. For these reasons, direct detection requires highly sensitive methods possessing broad spectrum specificity or a means of selecting specific organisms as described in U.S. Pat. No. 4,592,994. Because of the requirements of both high sensitivity and broad spectrum specificity, direct detection approaches such as immunoassays directed toward the cells or their products are subject to chemical interferences.

To circumvent these problems, some manner of sample treatment has been typically required to concentrate the small numbers of organisms present in field sample materials and to free them from interfering materials which prevent analysis or cause inaccurate or false results. Generally, treatment processes can involve centrifugation, membrane filtration or chemical precipitation steps.

Chemical treatment, diatomaceous earth (DE) filtration, and charcoal adsorption are used extensively for drinking water treatment and waste water processing (Linstedt et al., Water Research, 8 753–760 (1974). Studies of these large scale production processes have shown that the processes are effective in screening debris, grit removal, clarification and biofiltration. Depending on the plant operating parameters and efficiency, the resulting water filtrates can be essentially free of particulates and microorganisms.

Pilot plant tests reported by K. P. Lang'e et al., (J. Am. Water Works Assoc., 78, 76–84 (1986)), have shown that virtually 100% of the parasite *Giardia lamblia* cysts are removed by filtration through DE over a wide range of conditions. Smaller organisms, such as coliform bacteria can also be removed but removal is functional and dependent on the grade of DE. Diatomaceous earth filters have also been reported to remove heterotrophic bacteria from sea water (J. Illingworth, et al., Aquaculture, 17, 181–187 (1979). With the aid of chemical agents and coated DE, virus can also be filtered. R. De Leon et al., Wat. Res., 20, 583–587 (1986), showed that rotoviruses and f2 coliphages could not be removed by strictly mixed media filtration. However, the addition of small amounts of alum and coagulant polymer improved the effectiveness of viral removal. T. S. Brown et al., J. Am. Water Works Assoc. 66, 98–102 (1974), also confirmed the removal of viruses from water by DE filtration by removing T2 bacteriophages and polioviruses from it. However, the conditions for removing these viruses appeared to be virus specific and depended on the appropriate adjustment of pH and the selection of an effective DE coating.

Generally, DE filtration is applicable for waters that do not contain high concentrations of sediment or algae, both of which are likely to cause "binding" of the filter media resulting in increased back pressure and obstructed fluid flow. DE biofiltration by itself has thus not been applicable for samples containing high sediments content or mixed phase samples such as water/oil emulsions. (K. P. Lang'e et al., J. AWWA, 78, 76–84 (1986). For these reasons, DE biofiltration technology has been limited in practice to large industrial and municipal plants where consistency over water composition can be anticipated and careful control over the hydrodynamics of fluid flow and the DE bed parameters can be maintained. Such filtration is substantially useless in any attempt to isolate SRB from oil well samples; plugging of the filter occurs too quickly.

The primary mechanism of DE biofiltration is straining. Therefore, biofiltration processes must be carried out slowly with care being taken not to disturb the pore structure of the primary DE bed. This requires extensive equipment to provide control over the fluid hydraulics of the filtration process. Such equipment is impractical for analytical testing and field use.

A secondary mechanism of DE biofiltration is the adsorption of fine particles or colloids on which the microorganisms are secondarily adsorbed. The surface charges on the DE and the colloids in the water samples limit the efficiency of this process.

The use of chemicals added either directly to the water or in combination with DE filtration also has been employed to circumvent the difficulties of biofiltration processes. This physical/chemical treatment process relies on chemical coagulation followed by sedimentation to remove the suspended solids. Typically the use of aluminum or iron salts as coagulants achieves significant phosphorous and particle removal. Linstedt et al., Water Research, 8, 753–760 (1974), showed that the addition of alum and other chemical agents can effectively remove soluble phosphates, turbidity, bacteria and heavy metals from wastewater. Lee et al., Lab. Pract., 23, 297–298 (1974), demonstrated that chemical flocculation with aluminum potassium sulfate can be used efficiently to recover bacteria from cell culture fluids by sedimentation.

While chemical flocculation is an easily accommodated procedure, it is generally not used to harvest microorganisms for analytical determination. Flocculation processes are quantitatively dependent on concentration of flocculating agent, the amount of competing charged species present in the sample and the charge on the microorganism. If sample materials vary widely in the concentration of competing materials, the microorganisms can not be recovered reproducibly. Also, too much flocculating agent can prevent flocculation. Furthermore, flocculation reagents can react with or prevent the reaction of reagents required for the further analysis of the sample. Most importantly the flocculating agents can solubilize or alter the chemical composition of cells. In this way, the coagulation reagents can compromise the immunological reactivity of the microorganisms. For these reasons, the use of chemical additives has not been an effective means for collecting and recovering microorganisms and removing contaminating solutes from them.

U.S. Pat. No. 4,515,697 describes a method for flocculating microalgae or other organic particles without the addition of reagents. The method passes the solutions containing the microalgae or other organic particles which they wish to collect through a fixed granular layer at a rate which allows the microalgae or other organic particles to collect and flocculate, clogging the bed of granular material in the process. They disclose the use of sand, ceramics and particles of calcinated clay as the granular material. There is no indication how quantitative the collection is.

Likewise, WO 87/00199 discloses that diatomaceous earth has the ability to irreversibly entrap microbes or the like within the interior structure of the particle and uses diatomaceous earth to concentrate bacteria on fibrous materials. This enabled the bacteria to be cultured and enhanced biological and chemical reactions by them due to their concentration. The efficiency of the recovery of the bacteria was not disclosed.

And GB 2,189,317 describes the use of titanous hydroxide suspension to immobilize sulfate-reducing bacteria so that they could be detected by an ELISA method.

It is an object of the present invention to provide an inexpensive method to collect and recover microorganisms from environmental samples. The method must be capable of use in the field to facilitate the direct detection of microorganisms and (or) their products. It is a further object to provide the means for concentrating the organisms and freeing them of interfering solutes for immunoassay or other detection. It is a still further object to provide a means including apparatus to make use of inexpensive and commonly available biofiltration materials to accomplish the foregoing objectives.

SUMMARY OF THE INVENTION

Figure 1A:
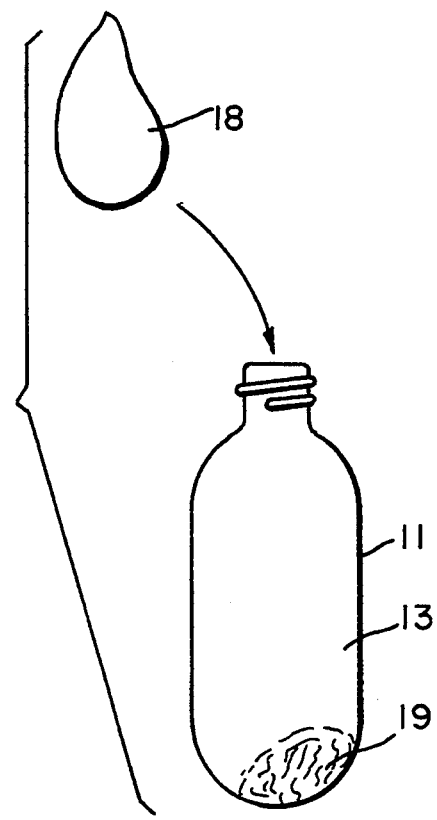
FIGS. 1A, 1B, 1C and 1D show the method of the invention including using the sample recovery device.

A method for collecting microorganisms from a sample comprising: mixing within a sample container, a sample and a sorbent in a fluid medium; shaking the mixture of and sample sorbent for microorganisims to suspend microorganisms and sorbent materials uniformly throughout the sample fluid; placing a sorbent collection cap on the sample container; expressing the sample fluids through the sorbent bed and sorbent collection cap; discarding the sample fluids; optionally, washing the "cake" of sorbent and entrapped and absorbed microorganisms in the sample recovery device; and, recovering the microorganism cells and their components collected and concentrated within the microbial sorbent by resuspending the cake particles and separating the microorganisms from the sorbent particles for detection and (or) analysis.

BEST MODE OF THE INVENTION

A method for collecting microorganisms from a 1–20 g sample containing less than 5% solids comprising: mixing within a sample container of from 3–10 times the sample volume, the sample and 10–60 mg of a sorbent composed of particles of diatomaceous earth (DE), perlite ($MgAlSiO_3$) or zeolite clays of alkali metal or hydrogen, at least 50% of the particles having a particle size from about 2 to about 10 microns, per ml of fluid in the sample. Specifically, the sorbent may be selected from Diatomaceous Earth Cat #1939-01 J. B. Baker, CELITE4/4, KENITE4/4 200, CELATOM4/4, CUNO4/4 M-901, CUNO4/4 m802, PERFLO4/4 200, PERFLO4/4 63, or PERFLO4/4 30. The next steps comprise shaking the sample-sorbent mixture 5–30 sec to suspend the microorganisms and sorbent particles substantially uniformly throughout the sample fluid; placing a sorbent collection cap on the sample container; expressing the sample fluids through the sorbent bed collected in the sorbent collection cap; discarding the sample fluids; optionally, washing the sorbent bed or cake in the sample recovery device with each wash fluid being about 10% of the original sample volume; and, recovering the cells collected usually by resuspending the particles of sorbent and cells and permitting the denser sorbent particles to settle and thus concentrating the microbes in the supernatant liquid for subsequent detection and (or) analysis.

DETAILED DESCRIPTION OF THE INVENTION

The method of this invention involves collecting microorganisms from a sample wherein the sample is first mixed with sorbent particles. The sorbent is a particulate material which either entraps or adsorbs microorganisms. Its pores are about 0.20 μm in diameter, through which the microorganisms do not pass. The sorbent should have a density greater than 1.0 g per cc. The specific sorbents that have operated successfully in this invention include J. T. Baker diatomaceous earth (cat. #1939-01), CELITE4/4, KENITE4/4 200, CELATOM4/4 FW6, CUNO4/4 M-901, CUNO4/4 m802, PERFLO4/4 200, PERFLO4/4 63, PERFLO4/4 30, ALITE4/4 150, ALITE4/4 180, or mixtures thereof. J. T. Baker diatomaceous earth (cat. # 1939-01), CELITE4/4, KENITE4/4 200, CELATOM4/4 FW6, CUNO4/4 M-901, CUNO4/4 m802, PERFLO4/4 200, PERFLO4/4 63, PERFLO4/4 30, are the preferred sorbents. A sample is defined as water, soil or other materials ranging from 0.5 to 100 g in weight, where 1 to 20 g is preferred. If the sample consists of dry or semi-solid substances, a suspending fluid is added to form a suspension containing less than 10% solids. However, less than 5% solids content is preferred. If the sample is essentially a liquid, the addition of suspending fluid is obviously not required. The fluid portion of a fluid-solid mixture is subsequently referred to as the sample fluid.

Figure 1B:
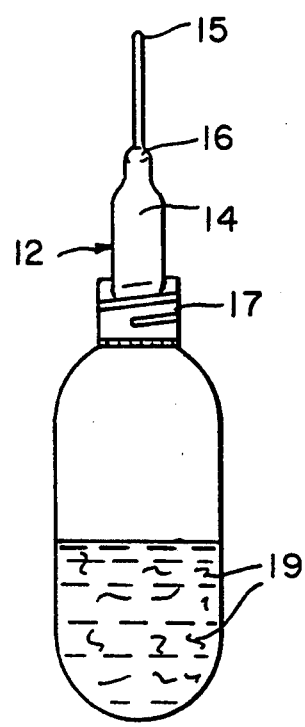
Figure 1C:
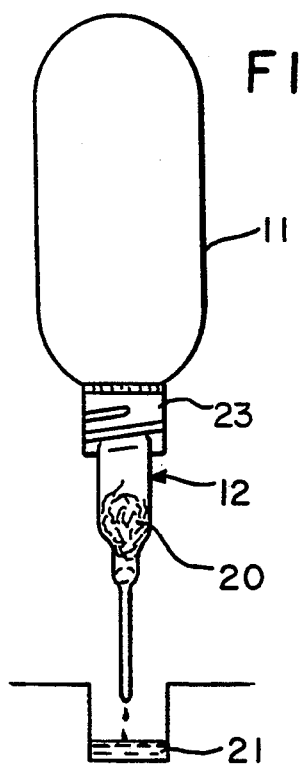
Figure 1D:
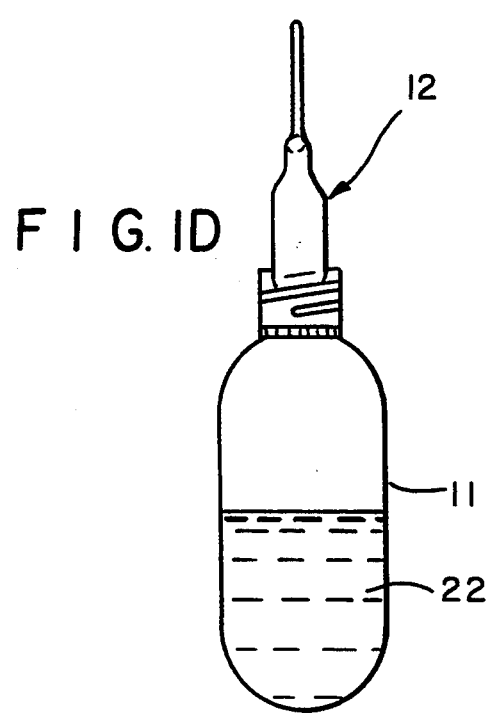

The method of this invention including using the sample recovery device is shown in FIGS. 1A, 1B, 1C and 1D. The sample device consists of two parts: the sample container and the sorbent collection cap. In FIGS. 1A, 1B, 1C and 1D, the sample container 11 consists of a flexible bulb 13 having a single opening adapted to provide a means to make an air-tight attachment with the sorbent collection cap 12. The sample container is adapted to enable quantitative transfer of sorbent solids to the cap. The volume of the bulbous compartment is from 2 to 20 times the sample volume with 3 to 10 times the volume being preferred. Prior to use, a microbial sorbent (or solvent(s)) is placed within the container.

The collection cap 12 consists of a hollow cone-shaped tube 14 with a narrow opening 15 at one end and a wider opening 17 at the other end. The top of the tube forms the narrow opening and means for holding a porous retainer 16, which may be polyethylene or other inert fibrous or the like material. The wider end of the tube 17 provides a means to make an air tight connection with the sample container 11 to serve as a means for containing sorbent and sample. The diameter of the narrow end 15 may be from 1.4 to 14 mm while 2.8 to 6.9 mm is preferred. The porous retainer 16 is placed within the narrow region of the tube and lodged there. The desired sample volumes, dictate the size of the tube for containing the sample and sorbent, Thus, the wide portion 17 of the cap, may range from 5.6 to 56 mm in diameter with 5.6 to 20.8 mm being preferred. The wide portion of the cap provides a compartment (containment chamber) 23 to collect sorbent and sample solids. The volume requirement for the containment chamber is 1.5 to 5 times the volume of sorbent solids.

The sample fluid 18 is placed in the sample container 11 as described above, then shaken with sorbent particles 19 to suspend any contained microorganisms and the sorbent materials uniformly throughout the sample fluid. Optionally, the sorbent materials can be used in mixtures. To enhance sorbent function, the sorbent particles can be surface treated by chemical coating or by graft polymerization. By these means, the surfaces of the sorbents can be modified to provide for suitable Zeta potential, ion exchange properties, Van der Waals forces for cell interaction or alteration of the surface properties such as wetting. While the amount of sorbent used depends on the size of the sample, there should be between 10 and 170 mg of sorbent per ml of sample fluid, preferably 10–60 mg per ml of sample fluid. Generally, during processing, an adequate suspension 19 of the sample can be accomplished by manually shaking the sample-sorbent mixture for 5 to 30 sec. depending on the type of sample and degree of agitation necessary to achieve suspension of the particular sorbent particles used.

A sorbent collection cap 12 is then attached to the sample container as in "B" and the sample recovery device is held with the tube end facing downward as in "C". The suspended materials are then allowed to partially settle, i.e., until a shallow bed of the sorbent ranging from 1 to 5 mm in depth is formed at the plug 20 in the tube. The sorbent, having the greater density, tends to settle first. Normally, this can be accomplished in 10 to 60 sec depending on the viscosity of the suspended sample and the density of the microbial sorbent. Longer settling times may be employed, however, with no reduction in the efficiency of microorganism collection.

The treated sample fluid 21 is forced through the sorbent bed by squeezing the sample container and this fluid is discarded. This step eliminates some of the soluble substances which might interfere with subsequent detection analyses. Wash fluids, if desired, can be drawn in and eluted through the sorbent bed 20. Generally, the volume of a wash fluid is equal to or less than the volume of the original sample fluid. However, smaller wash fluid volumes are preferred. Generally, wash fluid volumes of the order of 10% of the original sample fluid volume are effective in removing interfering solutes depending on the solute concentration and the mechanism of interference.

The organisms collected and concentrated within the sorbent bed 20 are transferred back to the sample container for detection and (or) analysis. Some fluid 22, termed "detection fluid", is first added. The sample recovery device is rotated so that the sample container 11 is below the cap 12 as in D and the device is then shaken to re-suspend the sorbent and the retained organisms in the fluid. If recovery of intact organisms is desired, the solids are allowed to settle out and the supernatant containing the resuspended organisms is removed by decanting after the sorbent collection cap is removed. In a preferred embodiment, where the detection of the intracellular or solubilized components of the organisms are of interest, the organisms in the detection fluid-sorbent mixture are lysed. The detection fluid 22 is then separated from the solids. This can be accomplished by squeezing the sample container to express the fluid through a sorbent collection cap. Lysis of the organisms can be accomplished by sonicating the sorbent-organism mixture in the detection fluid. Alternatively, the detection fluid can contain a lysing agent(s).

The method described in this invention, which uses particles of diatomaceous earth, DE, or similar sorbents, at least 50% of which have a particle size between 2 and 10 microns, and a specifically designed sample recovery device, results in the adequate capture of microorganisms, (at least 60%), the easy removal of interfering solutes, and the easy processing of the resulting microorganisms for their identification or analysis. Additionally, the method is quick, convenient for use in the field, and inexpensive.

EXAMPLES AND CONTROL

The following examples and control should aid in illustrating the overall utility of the sample processing method and the sample recovery device.

REAGENTS AND MATERIALS

Field Samples—Production oil well samples (about 1l) were obtained from Conoco North East Cherokee drilling field. Known numbers of bacteria of a pure strain of Desulfovibrio desulfuricans G100A, isolated from oilfield production water, were added to the samples.

Cell Detection—When the concentrations of SRB in the sample were sufficiently high, their cell number was confirmed by direct examination in a Petroff-Hauser counter using phase-contrast microscopy.

Usually, however, the concentrations of SRB were too low to be detected by direct microscopic examination. Therefore, they were determined indirectly using an immunoassay developed against the adenosine-5'-phosphosulfate (APS) reductase enzyme of SRB organisms as described in U.S. Pat. No. 4,895,795. The APS reductase is an intracellular enzyme found in all known SRB organisms. Prior to analysis, the samples were utrasonically treated for 90 sec (sonicated) to break open the bacterial cells and release the APS-reductase enzyme.

Test Buffer—TRIS BUFFER (50 mM, pH 7.5) Sodium Chloride (75 mM), 0.1% Low Foam Detergent (SL-18), BSA (0.1%), Azide (0.02%).

| | |
|---|---|
| TRIZMA* HCL (mwt. 157.6) | 6.35 gm |
| TRIZMA* BASE (mwt. 121.14) | 1.18 gm |
| Sodium Chloride (mwt. 58.45) | 4.38 gm |
| Bovine Serum Albumin | 1.00 gm |
| SL-18 Poly-Tergent4 4 | 1.0 ml |
| Sodium Azide | 0.20 gm |
| Purified Water | 1000 ml |

*Tris-hydroxy-methyl amino methane, manufactured by Sigma Chemical Corporation

The reagents were dissolved in water and the pH adjusted to between pH 7.4 and 7.6.

Wash Fluid—TRIS BUFFER (50 mM, pH 7.4), Azide (0.05%)

| | |
|---|---|
| TRIZMA* HCL | 6.61 GM |
| TRIZMA* BASE | 0.97 GM |
| Azide | 0.50 GM |

| | |
|---|---|
| -continued | |
| $H_2O$ | 1000 ML |

The pH of the solution is adjusted to between pH 7.3 and 7.4. The solution is filtered through a sterilizing filter and stored at 4° C.

PNP Chromogen Reagent

The reagent was prepared by mixing dissolved 0.1% p-nitrophenyl phosphate in diethanolamine buffer consisting of:

| | |
|---|---|
| diethanolamine | 97 ml |
| $MgCl_2$ | 0.1 g |
| sodium azide | 0.2 g |
| purified water | 1000 ml |

APS Reductase Immunoassay

A typical immunoassay test was accomplished by first adding 2.0 μl of a rabbit anti-APS alkaline phosphatase enzyme-antibody conjugate solution prepared according to the method described by Imagawa, J. Biochem., 92, 1413 (1982) to 0.2 ml of sample materials in test buffer. If the sample materials contained whole cells, the test mixture was first sonicated for 90 sec. The mixture was allowed to stand at room temperature for 3 min and then a single (4.0 mm in diameter) solid phase anti-APS antibody reagent bead was added and the mixture was agitated for 15 min at room temperature. The bead was then washed four successive times with 1.0 ml portions of fresh test buffer and then equilibrated with 0.5 ml of PNP chromogen reagent for 15 min at room temperature. The color which developed in the solution (0.2 ml) was measured in a Flow Laboratories (McLean, Va. 22102) microtiter plate reader at 405 nm.

CONTROL A

Influence of Field Samples on Direct SRB Detection

This control shows some of the difficulties encountered in isolating and detecting microorganisms in samples of oil fuild samples containing interfering substances.

Four aqueous samples obtained from oil production facilities and an additional sample from an industrial cooling tower were tested to determine the tolerance of SRB detection by the APS reductase immunoassay to the presence of chemicals and solids which might be present in the samples. The samples were tested directly and, also, after the removal of putative contaminants. These samples represented a variety of water types found at various stages of oil production, including injection water from waterflood fields, production water drawn directly from the wellheads and separated water phase from knockout drums. Each sample was seeded with SRB to contain concentrations of $2 \times 10^6$ cells per ml. A culture of SRB was also the source of one of the samples. As previously stated, to demonstrate the presence of potential interferring substances, each sample was tested both directly (i.e., without washing or other treatment) and after isolating and washing the cells present.

For direct testing, 0.2 ml of each sample was removed, sonicated for 90 sec and assayed for the concentration of SRB by means of the APS reductase immunoassay method described above. To prepare samples free of interfering materials, an additional 1.0 ml of each sample type was removed and passed through a 0.45 μm sterilizing membrane filter. The collected solid sediment was then rinsed off the filter by drawing 2.0 ml of test buffer through the filter and then backflushing the solids off of each filter using a strong pulse of 1.0 ml of test buffer. Portions (0.2 ml) of the filtered cell suspension were then removed, sonicated and tested for APS reductase by means of the APS reductase immunoassay. This is considered the Filter APS response in Table A. Portions (0.2 ml) of a culture of SRB were also tested using both treatment modes.

Comparison of the test results tabulated in Table A illustrate the presence of inhibitory materials in a large proportion of the field samples tested. The numbers represent the optical density readings of the APS reductase immunoassay perfomed as described above.

TABLE A

| Sample Type | Direct APS Response (O.D. 405 nm) | Filter APS Response (O.D. 405 nm) | % Change |
|---|---|---|---|
| Culture* | 0.95 | 1.00 | 5 |
| Oil Sample A | 0.79 | 1.19 | 34 |
| Oil Sample B | 0.77 | 1.34 | 43 |
| Oil Sample C | 1.14 | 1.10 | 4 |
| Oil Sample D | 0.80 | 1.26 | 34 |
| Cooling Water | 1.22 | 1.28 | 5 |

*Noninhibitory control sample taken from laboratory SRB culture fluid.

EXAMPLE 1

Collection and Recovery of Sulfate-reducing Bacteria (SRB) from Oil Well Production Water Samples From a non-inhibitory oil sample to which SRB had been added to a concentration of about $2 \times 10^6$ SRB per ml, 1.5 ml were added to 50 mg of J. T. Baker (Phillipsburg, N.J. 08865) diatomaceous earth (DE) (#1939-01). The mixtures were first shaken in the sample container for 15 sec and allowed to settle for about 1.0 min until a shallow DE bed had formed. The oily supernatant fluids were then expressed through the bed of DE and discarded.

To determine bacterial cell recovery, 1.5 ml of test buffer was added to the container; the cap was attached; and the recovered DE solids were recovered as a cake in the cap. The sorbent collection cap with the cake was then removed and the sample mixture was re-suspended and sonicated in the sample container for 90 sec to release the APS enzyme. The DE was then allowed to settle and 200 ul portions of the supernatant fluid containing the enzyme (detection fluid) were removed for testing by the APS reductase immunoassay method.

To determine the relative efficiency with which SRB were recovered, the results of the test samples described above were compared to control samples from which the SRB were first collected by filtration through a 0.45 μm sterilizing membrane filter and then recovered by backflushing the cells off the filter using a pressurized pulse of 1.5 ml of fresh test buffer. Portions (200 μl) of this solution were then sonicated for 90 sec and tested as above. This sample was labeled the control.

Portions of the seeded oil samples were tested directly in order to determine the 100% cell recovery (100% control).

The results tabulated below in Table 1 show that the DE biofiltration treatment was effective in the recovery of SRB cells from oil/water samples providing roughly equivalent cell recovery to the 0.45 μm sterilizing membrane filters.

TABLE 1

| Oil Sample | Treatment | Assay Result (O.D. 405 nm) | % Recovery |
|---|---|---|---|
| Test | DE | 1.39 | 77% |
| Control | 0.45 μm filter | 1.47 | 82% |
| 100% Control | none | 1.78 | 100% |

EXAMPLE 2

Influence of Sorbent Concentration on SRB Cell Recovery From Oil Well Samples

This example demonstrates that the amount of sorbent used to recover microorganisms from the fluids in which they are suspended influences the completeness of their recovery.

Varying amounts of diatomaceous earth, purchased from J. T. Baker, supra, (cat.#1939-1), were loaded into 7 of the sample recovery devices described above. Two ml portions of a liquid sample from a production oil well containing about $1 \times 10^6$ SRB cells/ml were then added to each sample recovery device. Samples were then processed and assayed by means of the APS reductase immunoassay as described above.

The results summarized in Table 2 demonstrate that sorbent concentration influences the efficiency of cell recovery. With oil well samples of this size, optimum recovery was achieved with between about 40 and about 80 mg of sorbent per ml of sample were used.

TABLE 2

| Diatomaceous Earth (mg/ml of sample) | Ave. Test Response (O.D. 405 nm) |
|---|---|
| 5 | 0.86 |
| 10 | 1.07 |
| 15 | 1.49 |
| 25 | 1.50 |
| 40 | 1.61 |
| 60 | 1.64 |
| 80 | 1.60 |
| 160 | 1.68 |

EXAMPLE 3

Cell Recovery at Varying SRB Cell Concentrations

The following example shows that microorganisms can be effectively recovered over a wide range of cell concentrations typically encountered in environmental samples.

In this example, production oil well samples were seeded with varying concentrations of SRB to concentrations of up to $0.5 \times 10^6$ cells/ml as described in the materials section. Using these samples, cell recovery was measured by use of the sorbent method of this invention with each sample recovery device containing 80 mg of sorbent per ml sample and also by filtration through a 0.45 μm sterilizing membrane filter.

To demonstrate the relative efficiency of recovery of both methods, control samples containing no inhibitor solutes were prepared by seeding 50 mM Tris buffer with the same cell concentrations as those in the seeded oil well samples. All the samples were sonicated for 90 sec, then assayed for APS reductase by means of the APS reductase immunoassay. Aliquots (1.5 ml) from the control samples were analyzed directly, without any treatment. The levels of APS reductase determined for the controls samples are considered to represent 100% of of detectable APS enzyme contained at each concentration of seeded SRB.

Cells were recovered from 1.5 ml samples of each of the different cell concentrations using the method of this invention. Cell recovery by means of the sterilizing membrane filters was determined by drawing 1.5 ml of each sample through a 0.45 μm sterilizing membrane filter (Gelman Sciences Inc., Ann Arbor, Mich. 48106). The recovered cells were then washed by drawing 2.0 ml of wash fluid through the filter. They were then removed from the filter for testing by using a strong back flush of 1.5 ml of sample buffer using a 10 ml syringe to move the fluids through the filter disc.

The results shown in Table 3 indicate cell recovery by the method of this invention is efficient at all cell concentrations tested. Recovery approached that achieved by sterilization membrane filtration and nearly 100% of the immunoassay-detectable APS reductase in the samples was measured. These results show that the microbial sorbent used in this invention not only gives excellent recovery of organisms but it also does not interfere with the test reagents or the analysis.

TABLE 3

INFLUENCE OF CELL CONCENTRATION ON CELL RECOVERY

| SRB Added (Cells/ml) | Control Samples (O.D. 405 nm) | Sorbent Method of Invention (O.D. 405 nm) | 0.45 μm Filter (O.D. 405) |
| --- | --- | --- | --- |
| $0.5 \times 10^7$ | 1.69 | 1.78 | 1.64 |
| $0.5 \times 10^6$ | 0.80 | 0.76 | 0.67 |
| $0.5 \times 10^5$ | 0.16 | 0.19 | 0.12 |
| $0.5 \times 10^4$ | 0.05 | 0.08 | 0.04 |
| 0 | 0.04 | 0.07 | 0.08 |

Numbers in the last 3 colums are the optical density readings at 405 nm used in the APS reductase immunoassay to determine APS reductase concentration. It should be noted that no test is sensitive at concentrations of $0.5 \times 10^4$ SRB cells/ml. or below.

EXAMPLE 4

Influence of Sorbent Type on SRB Cell Recovery

Sorbent materials (100 mg) of different types were loaded into sample recovery devices as described in example one. Culture fluids (2.0 ml) containing about $5 \times 10^8$ SRB per ml were added to each sample recovery devise and processed as in the previous examples. Following SRB collection on the sorbent materials, the number of SRB in the original samples and in filtrates into which SRB retained by the sorbent and then eluted from it were measured by direct cell counting using phase-contrast microscopy in a Petroff-Hauser counter. The result are shown in Table 4. Of the substances tested, those giving cell recoveries greater than 65% were considered adequate for the purposes of this invention. And, adequate cell recovery is obtained with a number of different sorbent materials. The types of DE, Perlites, and clays where particle size was such that at least 50% of the particles were between 2 and 10 microns give adequate (at least 60%) recovery of microorganisms for use in this invention.

TABLE 4

INFLUENCE OF SORBENT TYPE ON SRB RECOVERY

| Material Name (Microns) | Nature of the Material | % SRB Recovery | Particle Size |
| --- | --- | --- | --- |
| CELITE® (analytical filter a)[1] | Diatomaceous Earth | 88 | |
| KENITE® 200[2] | Diatomaceous Earth | 90 | 2-20 |
| KENITE® 700[2] | Diatomaceous Earth | 42 | 6-40 |
| KENITE® 3000[2] | Diatomaceous Earth | 00 | 10-40 |
| CELATOM® FW6[3] | Diatomaceous Earth | 61 | avg. 6 |
| CELATOM® FW60[3] | Diatomaceous Earth | 00 | avg. 19 |
| CELATOM® FW40[3] | Diatomaceous Earth | 39 | avg. 14 |
| CUNO® M-901[4] | Diatomaceous Earth | 66 | |
| CUNO® m802[4] | Diatomaceous Earth | 96 | |
| PERFLO® 200[5] | Perlite | 75 | |
| PERFLO® 63[5] | Perlite | 83 | |
| Perflo® 30[5] | Perlite | 81 | |
| Alite® 150[6] | Na Zeolite/clay | 86 | |
| Alite® 180[6] | H Zeolite/clay | 71 | |

[1] Details provided in "Tech Information Bulletin" of Johns Manville Corporation
[2] Details provided in "Tech Information Bulletin" of Witco Chemical Company
[3] Details provided in "Tech Information Bulletin" of Eagle Pitcher Company
[4] Details provided in "Tech Information Bulletin" of AMF/CUNO Microfiltration Products Co.
[5] Details provided in "Tech Information Bulletin" of Nord Resources Corp.
[6] Details provided in "Tech Information Bulletin" of Societe Chimique De La Grande Paroisse The invention being claimed is:

1. A method for separating and detecting bacteria from a heterogeneous environmental sample which comprises materials which interfere in detection of said bacteria, said method comprising the sequential steps of:
   (a) providing a substantially uniform suspension of said sample with particles in a first fluid, said particles being selected from the group consisting of diatomaceous earth, perlite and zeolite, at least 50% of said particles having a particle size between 2 and 10 microns and having a density greater than 1.0 g per cc;
   (b) forming a first liquid phase and a first solid phase from said suspension, wherein said solid phase comprises said particles and said bacteria;
   (c) removing said first liquid phase;
   (d) releasing said bacteria from said particles by forming a suspension of said first solid phase in a buffer solution,
   (e) forming a second liquid phase and a second solid phase from the suspension in step d), said second liquid phase comprising the buffer solution and said bacteria, and said second solid phase comprising said particles; and
   (f) detecting said bacteria from step e).

2. The method of claim 1 further comprising repeating sequential steps (a), (b), and (c) before step (d).

3. The method of claim 1 further comprising after step (e) disrupting said bacteria to release detectable intracellular components and detecting said intracellular components as an indication of said bacteria.

4. The method of claim 3 wherein said disrupting is accomplished by sonication.

5. The method of claim 1 wherein the bacteria are detected by immunoassay.

6. The method of claim 1 wherein said sample is an oil well sample and said bacteria are sulfate-reducing bacteria.

7. A method for collecting and separating bacteria for detection from a heterogeneous environmental sample which comprises materials which interfere in detection of said bacteria, said method comprising the sequential steps of:
   (a) providing a substantially uniform suspension of said sample with particles in a first fluid, said particles being selected from the group consisting of diatomaceous earth, perlite and zeolite, at least 50% of said particles having a particle size between 2 and 10 microns and having a density greater than 1.0 g per cc;
   (b) forming a first liquid phase and a first solid phase from said suspension, wherein said solid phase comprises said particles and said bacteria;
   (c) removing said first liquid phase;
   (d) releasing said bacteria from said particles by forming a suspension of said first solid phase in a buffer solution;
   (e) forming a second liquid phase and a second solid phase from the suspension in step d), said second liquid phase comprising the second fluid and said bacteria, and said second solid phase comprising said particles.

* * * * *